(12) United States Patent
Osei

(10) Patent No.: US 9,161,953 B2
(45) Date of Patent: Oct. 20, 2015

(54) GLP-1 RECEPTOR AGONISTS FOR ISLET CELL TRANSPLANTATION

(75) Inventor: Kwame Osei, San Diego, CA (US)

(73) Assignees: Amylin Pharmaceuticals, LLC, Wilmington, DE (US); Eli Lilly And Company, Indianapolis, IN (US)

( * ) Notice: Subject to any disclaimer, the term of this patent is extended or adjusted under 35 U.S.C. 154(b) by 0 days.

(21) Appl. No.: 13/996,093

(22) PCT Filed: Dec. 20, 2011

(86) PCT No.: PCT/US2011/066251
§ 371 (c)(1),
(2), (4) Date: Sep. 24, 2013

(87) PCT Pub. No.: WO2012/088157
PCT Pub. Date: Jun. 28, 2012

(65) Prior Publication Data
US 2014/0017208 A1 Jan. 16, 2014

Related U.S. Application Data

(60) Provisional application No. 61/426,076, filed on Dec. 22, 2010.

(51) Int. Cl.
| | | |
|---|---|---|
| A01N 63/00 | (2006.01) | |
| A61K 38/43 | (2006.01) | |
| A61K 35/39 | (2015.01) | |
| A61K 38/26 | (2006.01) | |
| A61K 38/16 | (2006.01) | |

(52) U.S. Cl.
CPC ............... *A61K 35/39* (2013.01); *A61K 38/16* (2013.01); *A61K 38/26* (2013.01)

(58) Field of Classification Search
None
See application file for complete search history.

(56) References Cited

U.S. PATENT DOCUMENTS

| | | | |
|---|---|---|---|
| 2006/0062769 A1 | 3/2006 | Habener et al. | |
| 2008/0287423 A1 | 11/2008 | Mussmann et al. | |
| 2009/0202494 A1* | 8/2009 | Cruz et al. | 424/93.7 |

OTHER PUBLICATIONS

Toso et al., Eur. Soc. Org. Trans., 23:259-265 (2010).*
Froud et al., Trans., 86(1):36-45 (2008).*
Toyoda et al., Biochem. Biophys. Res. Comm., 367:793-798 (2008).*
Berney, Eur. Soc. Org. Trans., 23:257-258 (2010).*
Faradji et al., Cell Trans., 18:124-71259 (2009).*
Rickels et al., Clin. Endocrinol. Metab., 94(1):181-189 (2009).*
International Search Report of PCT/US11/66251 mailed Jul. 2, 2012.
Merani et al., "Liraglutide, a long-acting human glucagon-like peptide 1 analog, improves glucose homeostasis in marginal mass islet transplantation in mice", Endocrinology (2008), vol. 149, p. 4322-4328.
King et al., "Islet transplantation outcomes in mice are better with fresh islets and exendin-4 treatment", Diabetologia (2005) vol. 48 (10), p. 2074-9.
Crutchlow et al., "Exendin-4 does not promote beta cell proliferation or survival during the early post-islet transplant period in mice", Transplant proc. (2008) vol. 40(5) p. 1650-1657, p. 1-15.
New York-Presbyterian Hospital/Weill Cornell Medical Center/Weill Cornell Medical College (Mar. 22, 2007). Sucessful Islet Cell Transplant Without Immunosuppressive Therapy in Mice With Type 1 Diabetes, Science Daily. Retried Sep. 16, 2013, from http://sciencedaily.com/releases/2007/03/070320074839.htm.
Luo et al., "Dentritic cells with TGF-β1 differentiate naïve CD4+CD25⁻ T cells into Islet-protective Foxp+ regulatory T cells", PNAS, Feb. 20, 2007, vol. 104, No. 8, pp. 2821-2826.
E.J. Verspohl, "Novel therapeutics for type 2 diabetes: Incretin hormone mimetics (glucagon-like peptide-1 receptor agonists) and dipeptidyl peptidase-4 inhibitors", Pharmacology & Therapeutics, vol. 124, pp. 113-138 (2009).
Su-Jin Kim et al., "Dipeptidyl Peptidase IV Inhibition With MK0431 Improves Islet Graft Survival in Diabetic NOD Mice Partially via T-Cell Modulation", Diabetes, col. 58, pp. 641-651, (Mar. 2009).
EP Search Report for EP 11 85 0148 dated Apr. 8, 2014.
Jill Buss et al., "Pre-Treatment with Exenatide in Islet Cell Transplantation Donors and Recipients Improves Graft Function in the Non-Human Primate", Diabetes, Abstract, (2009).
Jill L. Buss et al., "Exenatide Pre-Treatment Improved Islet Graft Function Compared to Treatment Post-Transplant Only", Diabetes, Abstract (2010).

* cited by examiner

*Primary Examiner* — Blaine Lankford
*Assistant Examiner* — Thomas J Visone
(74) *Attorney, Agent, or Firm* — Womble Carlyle Sandridge & Rice LLC

(57) ABSTRACT

The disclosure provides methods for treating diabetes by promoting graft survival and improved graft function in a patient receiving an islet transplant by treating the patient with a GLP-1 receptor agonist compound prior to the islet transplant. The methods may also comprise treating the islets with a GLP-1 receptor agonist compound prior to transplanting them in a patient. The methods may eliminate the need for immunosuppressive therapy in islet transplants. Any GLP-1 receptor agonist compound know in the art can be used in the methods described herein.

5 Claims, 5 Drawing Sheets

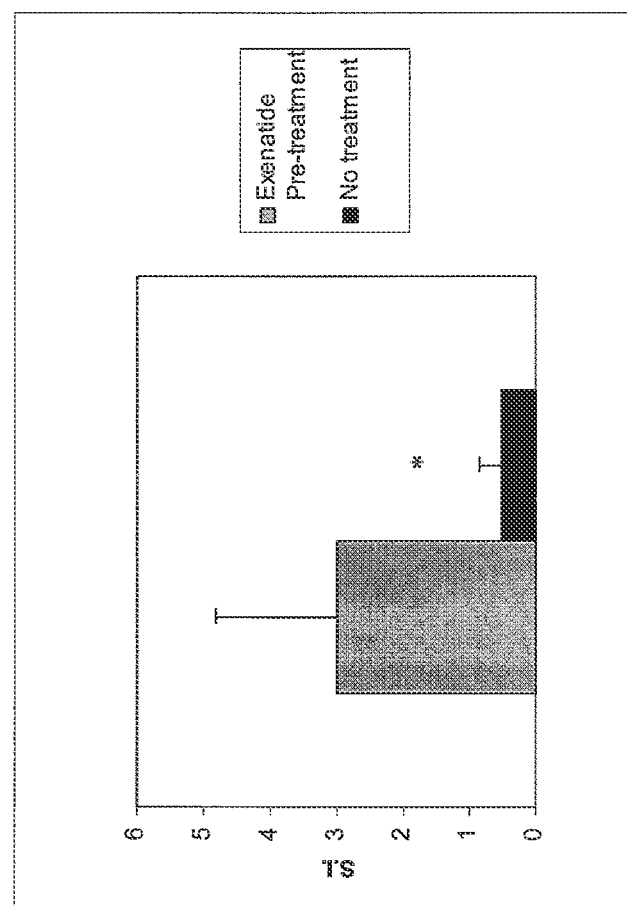

GLP-1 RECEPTOR AGONISTS FOR ISLET CELL TRANSPLANTATION

CROSS-REFERENCE TO RELATED APPLICATIONS

This application is a national phase of International Application No. PCT/US2011/066251, filed Dec. 20, 2011, which claims the benefit of priority to U.S. Provisional Application No. 61/426,076, filed on Dec. 22, 2010, the disclosure of each of which is incorporated herein by reference in its entirety.

FIELD

This disclosure is related to the use of glucagon-like peptide-1 (GLP-1) receptor agonists to improve the health and quality of life for people living with diabetes.

BACKGROUND

Type 1 diabetes has traditionally been treated by life-long insulin therapy or pancreas transplantation. However, frequent episodes of hypoglycemia are common in patients on life-long insulin therapy. And whole pancreas transplantation is an invasive surgical procedure with significant risks. Islet cell transplantation is an attractive alternative to the traditional treatments of type 1 diabetes. However, two of the major limiting factors in the widespread use of islet cell transplantation clinically are the availability of a sufficient number of islets and the inability of current immunosuppressive treatments to protect transplanted islets long-term.

As of 2005 an estimated 1.4 to 2.8 million people in the United States were diagnosed with insulin dependent diabetes (Collaborative Islet Transplant Registry, $5^{th}$ Annual Report, Bethesda, Md.: National Institutes of Diabetes and Digestive and Kidney Diseases, National Institutes of Health, 2008). According to a 2007 report by the United Network for Organ Sharing (UNOS), only 1,931 pancreatic donors were reported (United Network of Organ Sharing; Donors Recovered in the U.S. by Donor Type. Washington, D.C.: United States Department of Health and Human Services, 2009). Of those, 1,363 were used for whole pancreas transplantation. Because islet transplantation is still an experimental procedure, priority of donor pancreata goes to whole organ transplant. Thus, only 568 pancreata would have been available in 2007 for islet cell transplantation. In addition to this already limited availability of pancreata for islet transplantation, most islet transplant recipients require more than one donor in order to acquire a sufficient number of islet cells to achieve insulin independence. This limits the number of people who could be helped by islet cell transplantation even more. Alternative sources of islet cells or development of a method for β-cell regeneration are essential to the widespread use of islet transplantation in treating type 1 diabetes.

Despite using 2-3 pancreata for each recipient, however, results reported by the Edmonton group have shown that the rate of success for functional islet grafts in the clinical setting is approximately 80% after 1 year, but only 10% after 5 years (Ryan et al, *Diabetes*, 54(7):2060-2069 (2005); Shapiro et al, *N Engl J Med*, 343(4):230-238 (2000)). Effects of both auto- and allogeneic immune responses severely limit the long-term success of islet grafts, even when an abundant number of islets have been transplanted. Thus, development of an immunosuppressive treatment strategy that protects islets long-term is necessary for the overall success of this procedure.

Many immunosuppressive protocols used in islet cell transplantation to date have relied on calcineurin inhibitors that have been shown to negatively affect pancreatic β-cell function and insulin sensitivity. Therefore, despite offering protection from host immune attack, these agents themselves can diminish graft function and contribute to failure of the transplanted islets. Additionally, recipients of islet grafts still demonstrate the auto-immune effects of diabetes development that led to their disease initially, thereby affecting function of transplanted islets long-term.

GLP-1 receptor agonists (such as exenatide, lixisenatide, liraglutide, albiglutide, dulaglutide, taspoglutide) bind to the GLP-1 receptor on beta cells and have been shown to improve insulin secretion in response to glucose in addition to protecting beta cells from apoptosis and promoting beta cell regeneration in animals. Shalev et al, *Horm Res*, 49(5):221-225 (1998); Chen et al, *Biochem Biophys Res Comm*, 346:1067-1074 (2006); Xu et al, *Diabetes*, 48:2270-2276 (1998); Tourrel et al, *Diabetes*, 50:1562-1570 (2001); Couto et al, *Metabolism Clinical and Experimental*, 56:915-918 (2007). Studies in NOD mice have also shown that pre-treatment of islet recipients with a DPPIV-inhibitor can alter T-cell migration to islets. Kim et al, *Diabetes*, 58:641-651 (2009).

Because of the drawbacks of conventional immunosuppressive therapy, there is a need in the art for an effective form of treatment to allow for long-term islet graft function. The disclosure is directed to the unexpected discovery that GLP-1 receptor agonists can meet this need.

SUMMARY

It has not been previously shown whether treatment with GLP-1 receptor agonists will show protective properties in islet allotransplant recipients. We proposed and conducted studies that showed that pre-treatment of islet donors and/or recipients with GLP-1 receptor agonists promoted graft survival and improved graft function relative to post-transplant treatment alone. Moreover, this treatment method was successful without the use of immunosuppressive drugs.

In the example described herein, pancreatectomized cynomolgous monkeys underwent islet allotransplantation and were treated with the GLP-1 receptor agonist exenatide (5 mcg subcutaneous, twice daily) beginning on day 0 (n=3) or day −2 (n=3). A third group of animals (n=5) was treated with the immunosuppressive regimen of rabbit anti-thymocyte globulin, cyclosporine, and mycophenolate mofetil. A fourth group of animals remained untreated (n=4). Fasting blood glucose was measured daily and intravenous glucose tolerance tests were performed to evaluate graft function. The results showed that the average fasting blood glucose for pre-treated animals on day 5 post-transplant was 52.7±14.8 mg/dl while the average fasting blood glucose for animals treated with exenatide post-transplant only was 154.3±105.5 mg/dl. The day 5 average fasting blood glucose was 59.4 mg/dl±12.1 in animals treated with immunosuppression. Untreated animals had an average fasting blood glucose of 265.5±172.3 mg/dl. Beta cell function as determined by homeostasis model assessment notably improved post-transplant in exenatide pre-treated animals (53.3% vs. 107%) and marginally improved in animals treated with immunosuppression (29.9% vs. 43.8%) while a marked decrease was noted in untreated animals (20.2% vs. 1.89%) as well as animals treated with exenatide post-transplant only (22.2% vs. 13.8%). intravenous glucose tolerance tests showed normal glucose and insulin curves in the pre-treated exenatide and immunosuppression groups only. These studies unex-

BRIEF DESCRIPTION OF THE FIGURES

FIG. 4. In vitro static glucose stimulation assays performed on freshly isolated islets showed a significant improvement in Stimulation Index of insulin release for islets that had been pre-treated with exenatide in vivo compared to untreated islets. * p≤0.05

DETAILED DESCRIPTION

Figure 1:
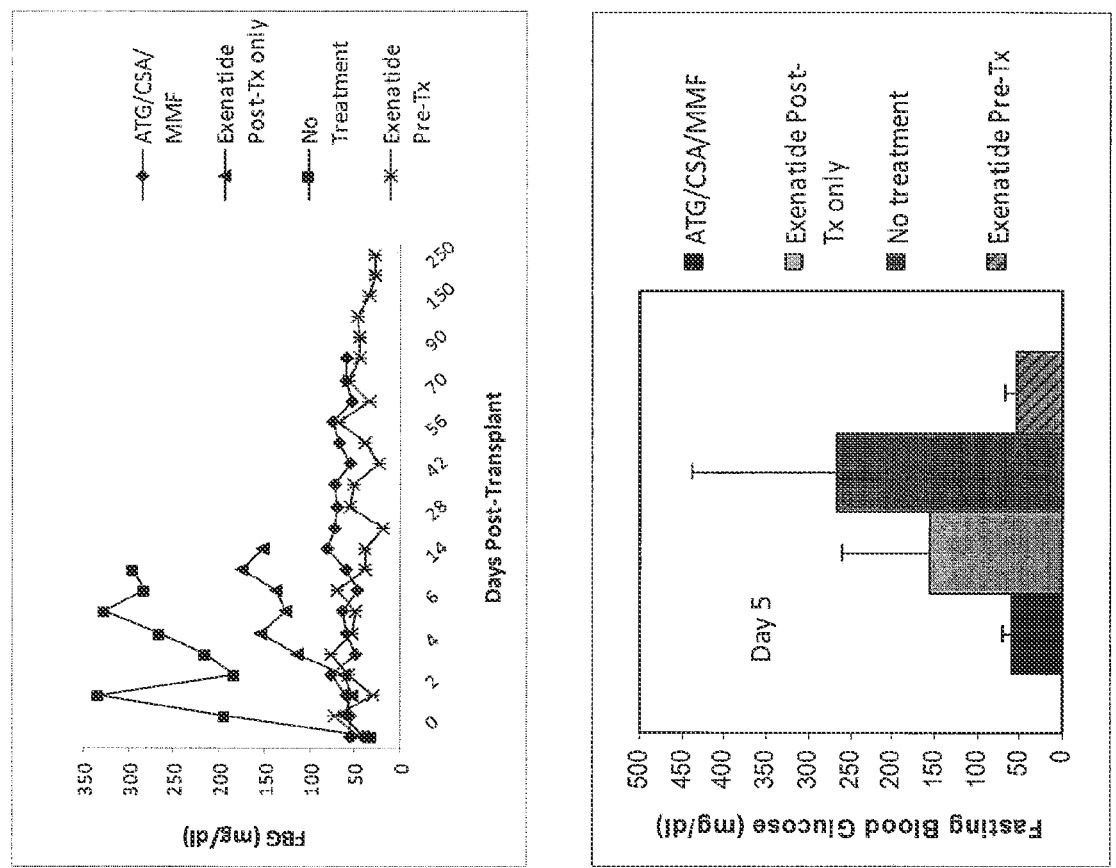
FIGS. 1A-B. Fasting blood glucose monitoring of transplanted animals (A). Average fasting blood glucose levels measured at day 5 post-transplant (B). Untreated animals showed elevated blood glucose levels by day 1 post-transplant, animals treated with exenatide post-transplant only showed somewhat elevated blood glucose levels beginning at day 4 post-transplant, while animals treated with ATG/CSA/MMF or pre-treated with exenatide remained normoglycemic throughout the study period. In fact, two animals from the exenatide pre-treatment group remained normoglycemic up to 435 days post-transplant.

The disclosure provides methods for treating diabetes in patients by administering therapeutically effective amounts of GLP-1 receptor agonist compound to the patient prior to islet transplant, and transplanting islets into the patient; thereby treating diabetes. In one embodiment, in the patient is not administered an immunosuppressive drug or an immunosuppressive treatment regimen before, during, or after the islet transplant. In one embodiment, the diabetes is Type 1 diabetes. In one embodiment, the patient is a human.

The disclosure provides method for treating diabetes in patients by administering therapeutically effective amounts of a GLP-1 receptor agonist compound to the patient for a period of time of 1 day to 1 month; treating islets with a therapeutically effective amount of a GLP-1 receptor agonist compound to the patient for a period of time of 1 day to 1 month; transplanting the islets into the patient; and continuing administration of the therapeutically effective amounts of the GLP-1 receptor agonist compound to the patient after the islet transplant; thereby treating diabetes in the patient. In one embodiment, in the patient is not administered an immunosuppressive drug or an immunosuppressive treatment regimen before, during, or after the islet transplant. In one embodiment, the diabetes is Type 1 diabetes. In one embodiment, the patient is a human.

The disclosure provides methods for promoting graft survival and improved graft function in a patient receiving an islet transplant by administering therapeutically effective amounts of a GLP-1 receptor agonist compound to the patient prior to islet transplant; transplanting the islets into the patient; and continuing administration of the therapeutically effective amounts of the GLP-1 receptor agonist compound to the patient after the islet transplant; thereby promoting graft survival and improved graft function in the patient. In one embodiment, the methods include treating islets with therapeutically effective amounts of a GLP-1 receptor agonist compound prior to transplant into the patient. In one embodiment, in the patient is not administered an immunosuppressive drug or an immunosuppressive treatment regimen before, during, or after the islet transplant. In one embodiment, the diabetes is Type 1 diabetes. In one embodiment, the patient is a human.

The disclosure provides methods for promoting graft survival and improved graft function in a patient receiving an islet transplant by administering a therapeutically effective amount of a GLP-1 receptor agonist compound to the patient for a period of time of 1 day to 1 month; treating islets with a therapeutically effective amount of a GLP-1 receptor agonist compound to the patient for a period of time of 1 day to 1 month; transplanting the islets into the patient; and continuing administration of therapeutically effective amounts of the GLP-1 receptor agonist compound to the patient after the islet transplant; thereby promoting graft survival and improved graft function in the patient. In one embodiment, in the patient is not administered an immunosuppressive drug or an immunosuppressive treatment regimen before, during, or after the islet transplant. In one embodiment, the diabetes is Type 1 diabetes. In one embodiment, the patient is a human.

Any GLP-1 receptor agonist compound can be used in the methods described herein, as set forth in more detail below.

A "GLP-1 receptor agonist compound" refers to compounds having GLP-1 receptor activity. Such exemplary compounds include exendins, exendin analogs, exendin agonists, GLP-1(7-37), GLP-1(7-37) analogs, GLP-1(7-37) agonists, and the like.

The term "exendin" includes naturally occurring (or synthetic versions of naturally occurring) exendin peptides that are found in the salivary secretions of the Gila monster. Exendins of particular interest include exendin-3 and exendin-4. The exendins, exendin analogs, and exendin agonists for use in the methods described herein may optionally be amidated, and may also be in an acid form, pharmaceutically acceptable salt form, or any other physiologically active form of the molecule.

Exendin-4 (HGEGTFTSDLSKQMEEEAVR-LFIEWLKNGGPSSGAPPPS-NH$_2$ (SEQ ID NO:1)) is a peptide found in the saliva of the Gila monster, *Heloderma suspectum*; and exendin-3 (HSDGTFTSDLSKQMEEEAVRLFIEWLKNGG PSS-GAPPPS-NH$_2$ (SEQ ID NO:2)) is a peptide found in the saliva of the beaded lizard, *Heloderma horridum*. Exendins have some amino acid sequence similarity to some members of the glucagon-like peptide (GLP) family. For example, exendin-4 has about 53% sequence identity with glucagon-like peptide-1(GLP-1)(7-37) (HAEGTFTSDVS- SYLEGQAAKEFIAWLVKGRG (SEQ ID NO:22)). However, exendin-4 is transcribed from a distinct gene, not the Gila monster homolog of the mammalian proglucagon gene from which GLP-1 is expressed. Additionally, exendin-4 is not an analog of GLP-1(7-37) because the structure of synthetic exendin-4 peptide was not created by sequential modification of the structure of GLP-1. Nielsen et al, *Current Opinion in Investigational Drugs,* 4(4):401-405 (2003).

Synthetic exendin-4, also known as exenatide, is commercially available as BYETTA® (Amylin Pharmaceuticals, Inc. and Eli Lilly and Company). BYETTA® contains exenatide, a preservative (e.g., metacresol), a tonicity-adjusting agent (e.g., mannitol), and a buffer (e.g., an acetate buffer). A once weekly formulation of exenatide is currently awaiting FDA approval and is described in WO 2005/102293, the disclosure of which is incorporated by reference herein. This once weekly formulation comprises exenatide and biodegradable polymeric (e.g., poly(lactide-co-glycolide)) microspheres, and is referred to herein as EQW (BYDUREON™ by Amylin Pharmaceuticals, Inc., Eli Lilly and Company, Alkermes, Inc.).

"Exendin analog" refers to peptides or other compounds which elicit a biological activity of an exendin reference peptide, preferably having a potency equal to or better than the exendin reference peptide (e.g., exendin-4), or within five orders of magnitude (plus or minus) of potency compared to the exendin reference peptide, when evaluated by art-known measures such as receptor binding and/or competition studies as described, e.g., by Hargrove et al, *Regulatory Peptides,* 141:113-119 (2007), the disclosure of which is incorporated by reference herein. Preferably, the exendin analogs will bind in such assays with an affinity of less than 1 μM, and more preferably with an affinity of less than 3 nM, or less than 1 nM. The term "exendin analog" may also be referred to as "exendin agonist".

Exendin analogs also include the peptides described herein which have been chemically derivatized or altered, for example, peptides with non-natural amino acid residues (e.g., taurine, β-amino acid residues, γ-amino acid residues, and D-amino acid residues), C-terminal functional group modifications, such as amides, esters, and C-terminal ketone modifications and N-terminal functional group modifications, such as acylated amines, Schiff bases, or cyclization, as found, for example, in the amino acid pyroglutamic acid. Exendin analogs may also contain other chemical moieties, such as peptide mimetics.

Exemplary exendins and exendin analogs include exendin-4 (SEQ ID NO:1); exendin-3 (SEQ ID NO:2); Leu$^{14}$-exendin-4 (SEQ ID NO:3); Leu$^{14}$,Phe$^{25}$-exendin-4 (SEQ ID NO:4); Leu$^{14}$,Ala$^{19}$,Phe$^{25}$-exendin-4 (SEQ ID NO:5); exendin-4(1-30) (SEQ ID NO:6); Leu$^{14}$-exendin-4(1-30) (SEQ ID NO:7); Leu$^{14}$,Phe$^{25}$-exendin-4(1-30) (SEQ ID NO:8); Leu$^{14}$,Ala$^{19}$,Phe$^{25}$-exendin-4(1-30) (SEQ ID NO:9); exendin-4(1-28) (SEQ ID NO:10); Leu$^{14}$-exendin-4(1-28) (SEQ ID NO:11); Leu$^{14}$,Phe$^{25}$-exendin-4(1-28) (SEQ ID NO:12); Leu$^{14}$,Ala$^{19}$,Phe$^{25}$-exendin-4 (1-28) (SEQ ID NO:13); Leu$^{14}$,Lys$^{17,20}$,Ala$^{19}$,Glu$^{21}$,Phe$^{25}$,Gln$^{28}$-exendin-4 (SEQ ID NO:14); Leu$^{14}$,Lys$^{17,20}$,Ala$^{19}$,Glu$^{21}$,Gln$^{28}$-exendin-4 (SEQ ID NO:15); octylGly$^{14}$,Gln$^{28}$-exendin-4 (SEQ ID NO:16); Leu$^{14}$,Gln$^{28}$,octylGly$^{34}$-exendin-4 (SEQ ID NO:17); Phe$^{4}$,Leu$^{14}$,Gln$^{28}$,Lys$^{33}$,Glu$^{34}$, Ile$^{35,36}$,Ser$^{37}$-exendin-4(1-37) (SEQ ID NO:18); Phe$^{4}$,Leu$^{14}$,Lys$^{17,20}$,Ala$^{19}$,Glu$^{21}$,Gln$^{28}$-exendin-4 (SEQ ID NO:19); Val$^{11}$,Ile$^{13}$,Leu$^{14}$,Ala$^{16}$,Lys$^{21}$,Phe$^{25}$-exendin-4 (SEQ ID NO:20); exendin-4-Lys$^{40}$ (SEQ ID NO:21); lixisenatide (Sanofi-Aventis/Zealand Pharma); CJC-1134 (ConjuChem, Inc.); [N$^{\epsilon}$-(17-carboxyheptadecanoic acid)Lys$^{20}$]exendin-4-NH$_2$; [N$^{\epsilon}$-(17-carboxyhepta-decanoyl)Lys$^{32}$]exendin-4-NH$_2$; [desamino-His$^{1}$,N$^{\epsilon}$-(17-carboxyheptadecanoyl)Lys$^{20}$]exendin-4-NH$_2$; [Arg$^{12,27}$,NLe$^{14}$,N$^{\epsilon}$-(17-carboxy-heptadecanoyl)Lys$^{32}$]exendin-4-NH$_2$; [N$^{\epsilon}$-(19-carboxy-nonadecanoylamino)Lys$^{20}$]-exendin-4-NH$_2$; [N-(15-carboxypentadecanoylamino)Lys$^{20}$]-exendin-4-NH$_2$; [N$^{\epsilon}$-(13-carboxytridecanoylamino)Lys$^{20}$]exendin-4-NH$_2$; [N$^{\epsilon}$-(11-carboxy-undecanoyl-amino)Lys$^{20}$]exendin-4-NH$_2$; exendin-4-Lys$^{40}$(8-MPA)-NH$_2$; exendin-4-Lys$^{40}$($\epsilon$-AEEA-AEEA-MPA)-NH$_2$; exendin-4-Lys$^{40}$($\epsilon$-AEEA-MPA)-NH$_2$; exendin-4-Lys$^{40}$($\epsilon$-MPA)-albumin; exendin-4-Lys$^{40}$($\epsilon$-AEEA-AEEA-MPA)-albumin; exendin-4-Lys$^{40}$($\epsilon$-AEEA-MPA)-albumin; and the like. AEEA refers to [2-(2-amino)ethoxy)]ethoxy acetic acid. EDA refers to ethylenediamine. MPA refers to maleimidopropionic acid. The exendins and exendin analogs may optionally be amidated.

Other exendins and exendin analogs useful in the methods described herein include those described in WO 98/05351; WO 99/07404; WO 99/25727; WO 99/25728; WO 99/40788; WO 00/41546; WO 00/41548; WO 00/73331; WO 01/51078; WO 03/099314; U.S. Pat. No. 6,956,026; U.S. Pat. No. 6,506,724; U.S. Pat. No. 6,703,359; U.S. Pat. No. 6,858,576; U.S. Pat. No. 6,872,700; U.S. Pat. No. 6,902,744; U.S. Pat. No. 7,157,555; U.S. Pat. No. 7,223,725; U.S. Pat. No. 7,220,721; U.S. Publication No. 2003/0036504; and U.S. Publication No. 2006/0094652, the disclosures of which are incorporated by reference herein in their entirety.

"GLP-1(7-37) analogs" refers to peptides or other compounds which elicit a biological activity similar to that of GLP-1(7-37), when evaluated by art-known measures such as receptor binding assays or in vivo blood glucose assays as described, e.g., by Hargrove et al, *Regulatory Peptides,* 141:113-119 (2007), the disclosure of which is incorporated by reference herein. In one embodiment, the term "GLP-1(7-37) analog" refers to a peptide that has an amino acid sequence with 1, 2, 3, 4, 5, 6, 7 or 8 amino acid substitutions, insertions, deletions, or a combination of two or more thereof, when compared to the amino acid sequence of GLP-1(7-37). In one embodiment, the GLP-1(7-37) analog is GLP-1(7-36)-NH$_2$. GLP-1(7-37) analogs include the amidated forms, the acid form, the pharmaceutically acceptable salt form, and any other physiologically active form of the molecule.

Exemplary GLP-1(7-37) and GLP-1(7-37) analogs include GLP-1(7-37) (SEQ ID NO:22); GLP-1(7-36))-NH$_2$ (SEQ ID NO:23); liraglutide (VICTOZA® from Novo Nordisk); dulaglutide (LY2189265, a GLP-1 analog linked to an immunoglobulin G4 by Eli Lilly and Company); albiglutide (SYNCRIA® from GlaxoSmithKline); taspoglutide (Hoffman La-Roche); dulaglutide (LY2189265, a GLP-1 analog linked to an immunoglobulin G4 by Eli Lilly and Company); LY2428757 (a GLP-1 analog linked to a polyethylene glycol by Eli Lilly and Company); desamino-His$^{7}$,Arg$^{26}$,Lys$^{34}$(N$^{\epsilon}$-(γ-Glu(N-α-hexadecanoyl)))-GLP-1(7-37); desamino-His$^{7}$,Arg$^{26}$,Lys$^{34}$(N$^{\epsilon}$-octanoyl)-GLP-1(7-37); Arg$^{26,34}$,Lys$^{38}$(N$^{\epsilon}$-(ω-carboxypentadecanoyl))-GLP-1(7-38); Arg$^{26,34}$,Lys$^{36}$(N$^{\epsilon}$-(γ-Glu(N-α-hexadecanoyl)))-GLP-1(7-36); Aib$^{8,35}$,Arg$^{26,34}$,Phe$^{31}$-GLP-1(7-36)) (SEQ ID NO:24); HXaa$_8$EGTFTSDVSSYLEXaa$_{22}$Xaa$_{23}$AAKEFIXaa$_{30}$WLXaa$_{33}$Xaa$_{34}$G Xaa$_{36}$Xaa$_{37}$; wherein Xaa$_8$ is A, V, or G; Xaa$_{22}$ is G, K, or E; Xaa$_{23}$ is Q or K; Xaa$_{30}$ is A or E; Xaa$_{33}$ is V or K; Xaa$_{34}$ is K, N, or R; Xaa$_{36}$ is R or G; and Xaa$_{37}$ is G, H, P, or absent (SEQ ID NO:25); Arg$^{34}$-GLP-1(7-37) (SEQ ID NO:26); Glu$^{30}$-GLP-1(7-37) (SEQ ID NO:27); Lys$^{22}$-GLP-1(7-37) (SEQ ID NO:28); Gly$^{8,36}$,Glu$^{22}$-GLP-1(7-37) (SEQ ID NO:29); Val$^{8}$,Glu$^{22}$,Gly$^{36}$-GLP-1(7-37) (SEQ ID NO:30); Gly$^{8,36}$,Glu$^{22}$,Lys$^{33}$,Asn$^{34}$-GLP-1(7-37) (SEQ ID NO:31); Val$^{8}$,Glu$^{22}$,Lys$^{33}$,Asn$^{34}$,Gly$^{36}$-GLP-1(7-37) (SEQ ID NO:32); Gly$^{8,36}$,Glu$^{22}$,Pro$^{37}$-GLP-1(7-37) (SEQ ID NO:33); Val$^8$,Glu$^{22}$,Gly$^{36}$Pro$^{37}$-GLP-1(7-37) (SEQ ID NO:34); Gly$^{8,36}$,Glu$^{22}$,Lys$^{33}$, Asn$^{34}$,Pro$^{37}$-GLP-1(7-37) (SEQ ID NO:35); Val$^8$, Glu$^{22}$,Lys$^{33}$,Asn$^{34}$,Gly$^{36}$,Pro$^{37}$-GLP-1(7-37) (SEQ ID NO:36); Gly$^{8,36}$,Glu$^{22}$-GLP-1(7-36) (SEQ ID NO:37); Val$^8$,Glu$^{22}$,Gly$^{36}$-GLP-1(7-36) (SEQ ID NO:38); Val$^8$,Glu$^{22}$,Asn$^{34}$,Gly$^{36}$-GLP-1(7-36) (SEQ ID NO:39); Gly$^{8,36}$,Glu$^{22}$,Asn$^{34}$-GLP-1(7-36) (SEQ ID NO:40). Each of the GLP-1(7-37) and GLP-1(7-37) analogs may optionally be amidated.

In one embodiment, the GLP-1(7-37) or GLP-1(7-37) analogs are covalently linked (directly or by a linking group) to an Fc portion of an immunoglobulin (e.g., IgG, IgE, IgG, and the like). For example, any one of SEQ ID NOs:25-40 may be covalently linked to the Fc portion of an immunoglobulin comprising the sequence of: AESKYGPPCPPCPAPXaa$_{16}$ Xaa$_{17}$Xaa$_{18}$GGPSVFLFPPKPKDTLMISRTPEVTCVVVD VSQEDPEVQFNWYVDGVEVHNAKTKPREEQFXaa$_{80}$ STYRVVSVLTVLHQDWLNGKEYKCKVSNKGLPSS IEKTISKAKGQPREPQVYTLPPSQEEMTKNQVSLTCL VKGFYPSDIAVEWESNGQPENNYKTTPPVLDSDGS FFLYSRLTVDKSRWQEGNVFSCSVMHEALHNHY TQKSLSLSLGXaa$_{230}$; wherein Xaa$_{16}$ is P or E; Xaa$_{17}$ is F, V or A; Xaa$_{18}$ is L, E or A; Xaa$_{80}$ is N or A; and Xaa$_{230}$ is K or absent (SEQ ID NO:41). The linking group may be any chemical moiety (e.g., amino acids and/or chemical groups). In one embodiment, the linking group is (-GGGGS-)$_x$ (SEQ ID NO:42) where x is 1, 2, 3, 4, 5 or 6; preferably 2, 3 or 4; more preferably 3. In one embodiment, the GLP-1(7-37) analog covalently linked to the Fc portion of an immunoglobulin comprises the amino acid sequence: HGEGTFTSDVS-SYLEEQAAKEFIAWLVKGGGGGGGSGGGGSGGG GS AESKYGPPCPPCPAPEAAGGPSVFLFPPKPKDTLMIS RTPEVTCVVVDVSQEDPEVQ FNWYVDGVEVHNAK-TKPREEQFNSTYRVVSVLTVLHQDWLNGKEYKCKV SNKGLPSSIEKTISKAKGQPREPQVYTLPPSQEEMTK NQVSLTCLVKGFYPSDIAVEWESN GQPENNYKTTP-PVLDSDGSFFLYSRLTVDKSRWQEGNVF-SCSVMHEALHNHYTQ KSLSLSLG (SEQ ID NO:43).

In another embodiment, the GLP-1(7-37) or GLP-1(7-37) analog may be covalently linked (directly or through a linking group) to one or two polyethylene glycol molecules. For example, a GLP-1(7-37) analog may comprise the amino acid sequence: HXaa$_8$EGTFTSDVS SYLEXaa$_{22}$QAA KEFIAWLXaa$_{33}$KGGPSSGAPPPC$_{45}$C$_{46}$-Z, wherein Xaa$_8$ is: D-Ala, G, V, L, I, S or T; Xaa$_{22}$ is G, E, D or K; Xaa$_{33}$ is: V or I; and Z is OH or NH$_2$, (SEQ ID NO:44), and, optionally, wherein (i) one polyethylene glycol moiety is covalently attached to C$_{45}$, (ii) one polyethylene glycol moiety is covalently attached to C$_{46}$, or (iii) one polyethylene glycol moiety is attached to C$_{45}$ and one polyethylene glycol moiety is attached to C$_{46}$. In one embodiment, the GLP-1(7-37) analog is HVEGTFTSDVSSYLEEQAAKEFIAWL IKGGPSSGAPPPC$_{45}$C$_{46}$-NH$_2$ (SEQ ID NO:45) and, optionally, wherein (i) one polyethylene glycol moiety is covalently attached to C$_{45}$, (ii) one polyethylene glycol moiety is covalently attached to C$_{46}$, or (iii) one polyethylene glycol moiety is attached to C$_{45}$ and one polyethylene glycol moiety is attached to C$_{46}$.

GLP-1 receptor agonist compounds may be prepared by processes well known in the art, e.g., peptide purification as described in Eng et al, *J. Biol. Chem.*, 265:20259-62 (1990); standard solid-phase peptide synthesis techniques as described in Raufman et al, *J. Biol. Chem.*, 267:21432-37 (1992); recombinant DNA techniques as described in Sambrook et al, Molecular Cloning: A Laboratory Manual, 2d Ed., Cold Spring Harbor (1989); and the like.

The disclosure also provides pharmaceutical compositions comprising the GLP-1 receptor agonist compounds described herein and a pharmaceutically acceptable carrier. The GLP-1 receptor agonist compounds can be present in the pharmaceutical composition in a therapeutically effective amount and can be present in an amount to provide a minimum blood plasma level of the GLP-1 receptor agonist compound necessary for therapeutic efficacy. Such pharmaceutical compositions are known in the art and described, e.g., in U.S. Pat. No. 7,521,423; U.S. Pat. No. 7,456,254; WO 2000/037098; WO 2005/021022; WO 2005/102293; WO 2006/068910; WO 2006/125763; WO 2009/068910; U.S. Publication No 2004/0106547; and the like, the disclosures of which are incorporated herein by reference.

Pharmaceutical compositions containing the GLP-1 receptor agonist compounds described herein may be provided for peripheral administration, such as parenteral (e.g., subcutaneous, intravenous, intramuscular), a continuous infusion (e.g., intravenous drip, intravenous bolus, intravenous infusion), topical, nasal, or oral administration. Suitable pharmaceutically acceptable carriers and their formulation are described in standard formulation treatises, such as Remington's Pharmaceutical Sciences by Martin; and Wang et al, Journal of Parenteral Science and Technology, Technical Report No. 10, Supp. 42:2S (1988).

The GLP-1 receptor agonist compounds described herein can be provided in parenteral compositions for injection or infusion. They can, for example, be suspended in water; an inert oil, such as a vegetable oil (e.g., sesame, peanut, olive oil, and the like); or other pharmaceutically acceptable carrier. In one embodiment, the compounds are suspended in an aqueous carrier, for example, in an isotonic buffer solution at a pH of about 3.0 to 8.0, or about 3.0 to 5.0. The compositions may be sterilized by conventional sterilization techniques or may be sterile filtered. The compositions may contain pharmaceutically acceptable auxiliary substances as required to approximate physiological conditions, such as pH buffering agents. Useful buffers include for example, acetic acid buffers. A form of repository or "depot" slow release preparation may be used so that therapeutically effective amounts of the preparation are delivered into the bloodstream over many hours or days following subcutaneous injection, transdermal injection or other delivery method. The desired isotonicity may be accomplished using sodium chloride or other pharmaceutically acceptable agents such as dextrose, boric acid, sodium tartrate, propylene glycol, polyols (such as mannitol and sorbitol), or other inorganic or organic solutes. In one embodiment for intravenous infusion, the formulation may comprise (i) the GLP-1 receptor agonist compound, (2) sterile water, and, optionally (3) sodium chloride, dextrose, or a combination thereof.

Carriers or excipients can also be used to facilitate administration of the GLP-1 receptor agonist compounds. Examples of carriers and excipients include calcium carbonate, calcium phosphate, various sugars such as lactose, glucose, or sucrose, or types of starch, cellulose derivatives, gelatin, vegetable oils, polyethylene glycols and physiologically compatible solvents.

The GLP-1 receptor agonist compounds can also be formulated as pharmaceutically acceptable salts (e.g., acid addition salts) and/or complexes thereof. Pharmaceutically acceptable salts are non-toxic salts at the concentration at which they are administered. Pharmaceutically acceptable salts include acid addition salts such as those containing sulfate, hydrochloride, phosphate, sulfamate, acetate, citrate, lactate, tartrate, methanesulfonate, ethanesulfonate, benzenesulfonate, p-toluenesulfonate, cyclohexylsulfamate and quinate. Pharmaceutically acceptable salts can be obtained from acids such as hydrochloric acid, sulfuric acid, phosphoric acid, sulfamic acid, acetic acid, citric acid, lactic acid, tartaric acid, malonic acid, methanesulfonic acid, ethanesulfonic acid, benzenesulfonic acid, p-toluenesulfonic acid, cyclohexylsulfamic acid, and quinic acid. Such salts may be prepared by, for example, reacting the free acid or base forms of the product with one or more equivalents of the appropriate base or acid in a solvent or medium in which the salt is insoluble, or in a solvent such as water which is then removed in vacuo or by freeze-drying or by exchanging the ions of an existing salt for another ion on a suitable ion exchange resin.

Exemplary pharmaceutical formulations of GLP-1 receptor agonist compounds are described in U.S. Pat. No. 7,521,423, U.S. Pat. No. 7,456,254; U.S. Publication No 2004/0106547, WO 2006/068910, WO 2006/125763, and the like, the disclosures of which are incorporated by reference herein.

The therapeutically effective amount of the GLP-1 receptor agonist compounds described herein for use in the methods described herein will typically be from about 0.01 µg to about 5 mg; about 0.1 µg to about 2.5 mg; about 1 µg to about 1 mg; about 1 µg to about 50 µg; or about 1 µg to about 25 µg. Alternatively, the therapeutically effective amount of the GLP-1 receptor agonist compounds may be from about 0.001 µg to about 100 µg based on the weight of a 70 kg patient; or from about 0.01 µg to about 50 µg based on the weight of a 70 kg patient. These therapeutically effective doses may be administered once/day, twice/day, thrice/day, once/week, biweekly, or once/month, depending on the formulation. The exact dose to be administered is determined, for example, by the formulation, such as an immediate release formulation or an extended release formulation. For transdermal, nasal or oral dosage forms, the dosage may be increased from about 5-fold to about 10-fold.

EXAMPLE

Materials and Methods

Animals:

Cynomolgous monkeys (*Macaca fascicularis*), aged 2-4 years, were obtained from Charles River Laboratories (Houston, Tex.) or Covance Research (Alice, Tex.). Animals had a starting weight of 4.35 kg±1.00 (range 2.5-6.1). Animals were housed in individual cages (28×30×24 in) and given a continuous water supply. Animals were fasted for 12 hours prior to surgery and intravenous glucose tolerance tests, but were otherwise fed with a regular primate diet supplemented with fresh produce. The procedures described in this study were conducted according to the guidelines set forth in the "Guide for the Care and Use of Laboratory Animals" and by the Institutional Animal Care and Use Committee (IACUC) and University Laboratory Animal Resources (ULAR) (Guide for the Care and Use of Laboratory Animals, 7th Ed. Washington D.C.: National Academy Press (1996)). The studies were conducted at Ohio State University, where the animal care program is accredited by AAALAC, Int.

Study Design:

All animals underwent total pancreatectomies to induce diabetes and were transplanted with islet allografts. The average dose of islets transplanted was 12,110 IEq/kg±7442.8. (IEq is Islet equivalent.) Group 1 (n=3) was treated with 5 µg exenatide twice daily (Amylin Pharmaceuticals, Inc., San Diego, Calif.) subcutaneously two days before (i.e., days −2) to the study endpoint, where day 0 was the day of transplant. Group 2 (n=3) was also treated with exenatide (5 µg twice daily subcutaneous) to study endpoint, but beginning on the day of transplant (i.e., day 0). Group 3 (n=5) was treated with an immunosuppression regimen: induction therapy consisted of rabbit antithymocyte globulin (ATG) (Thymoglobulin®, Genzyme, Cambridge, Mass.) at a dose of 1.5 mg/kg intravenously on days 0-3 and prednisone (Solu-medrol®, Pfizer, New York, N.Y.) tapered from 25-5 mg over days 0-3. Immunosuppression maintenance consisted of 25 mg cyclosporine (CSA) (Neoral®, Novartis, East Hanover, N.J.) and 250 mg mycophenolate mofetil (MMF) (CellCept®, Roche, Nutley, N.J.) given orally from day 0 to the study endpoint. Group 4 (n=4) was untreated and served as the control group.

Surgical Procedures:

Mismatched pairs of animals were placed under general anesthesia with isoflurane. A midline laparotomy was made in order to perform a total pancreatectomy. The pancreas was dissected from the splenic artery and vein, the portal vein and the duodenum with preservation of the spleen and common bile duct. Blood supply between the spleen and duodenum was double ligated, and the pancreas removed for islet isolation. Animals were maintained under anesthesia during the islet isolation with blood glucose monitoring completed every 15 minutes to ensure normoglycemia. Isolated islets from a mismatched allogeneic donor were immediately transplanted into the recipient pancreaectomized animal. For Group 1, both donor and recipient animals were pretreated with exenatide for 2 days prior to pancreatectomy and transplantation. Recipients from Groups 2, 3 and 4 received islets that had not been pretreated. The mesenteric vein was located and cannulated with an 18 gauge angiocatheter toward the portal vein. Islets suspended in 50 mL CMRL-1066 transplant media (Mediatech, Herndon, Va.) without heparin were slowly injected over 10 minutes. The catheter was removed and the vein ligated. The incision was closed, and animals recovered under close observation until conscious. Buprenex® (0.05 mg/kg, Reckitt Benckiser, Berkshire, UK) was given as a post-operative analgesic.

Islet Isolation:

Islet isolation was performed according to the modified human islet isolation protocol described by Rajab et al, *Cell Transplantation*, 17(9):1015-1023 (2008). Islet number was determined by dithizone staining and conversion to islet equivalents (IEq).

Post-Transplant Follow-Up:

For the first 48 hours post-transplant, blood glucose was measured twice daily using the tail prick method. A 10 µl drop of blood was drawn from the animal's tail for measurement on a standard glucometer (Ascensia Elite®, Bayer Healthcare, Mishawaka, Ind.). Fasting blood glucose was then measured once daily through day 7 post-transplant and weekly thereafter (for animals that were normoglycemic). Fasting blood glucose was measured prior to feeding the animals in the morning. Animals with a fasting blood glucose measuring 300 mg/dl or greater were monitored daily and given 2 units of NPH insulin (Eli Lilly, Indianapolis, Ind.). Intravenous glucose tolerance tests were performed prior to pancreatectomy on day 0 and post-transplant on days 10 and 90. The study endpoint was considered 90 days post-transplant for Groups 1-3 and 10 days post-transplant for the untreated Group 4 (due to the poor health noted by day 10 of animals in Group 4). However, two animals in group 1 (exenatide pretreatment) were monitored beyond 90 days and an additional intravenous glucose tolerance test was performed on day 220. Body weights for animals were monitored throughout the study.

Intravenous Glucose Tolerance Test:

Animals were fasted 12 hours prior to each intravenous glucose tolerance test. Baseline glucose and insulin were measured at times −5 and 0. A 50% solution of glucose was administered i.v. at time 0. Blood was drawn at times 1, 3, 5, 10, 15, 20, 25 and 30 minutes after glucose administration for measurement of blood glucose and serum insulin levels.

In Vitro Glucose Stimulation Assay:

Freshly isolated islets were handpicked (n=5 islets per replicate×3 replicates) and incubated at 37° C. in either "high" (16.7 mM) glucose or "low" (1.67 mM) glucose for 1 hour. Supernatants were collected by centrifugation and measured for insulin content using an ELISA kit for human insulin (Dako, Carpinteria, Calif.). An insulin stimulation index (S.I.=high/low glucose insulin release) was determined for each sample.

Data Analysis:

Area under the curve (AUC) was determined for all intravenous glucose tolerance test glucose curves. Glucose disappearance rate constants ($k_G$) were used as a measure of glucose tolerance and insulin sensitivity for intravenous glucose tolerance tests. $k_G$ was calculated as the negative slope of the linear regression for the natural logarithm of glucose from 10-30 minutes. Acute insulin response to glucose (AIRg) was used as a measure of first phase insulin secretion during intravenous glucose tolerance tests. AIRg was calculated as the mean of insulin at time 3-5 minutes minus the mean at time 0. Beta cell function was measured by the mathematical assessment of glucose regulation called the homeostasis model assessment (HOMA-% B). HOMA-% B was calculated as the average basal insulin (μIU/mL) multiplied by 20 and divided by the average basal glucose (mmol/mL) minus 3.5.

Statistical Analysis:

All results are expressed as mean±SEM unless otherwise stated. Student t-test and two-way analysis of variants (ANOVA) were used for parametric analysis. A probability value (p) of less than 0.05 is considered statistically significant.

Results

Fasting Blood Glucose:

Animals in the untreated control group showed elevated blood glucose levels by day 1 post-transplant (FIG. 1A), with the average fasting blood glucose at day 5 post-transplant being 265 mg/dl±172 (FIG. 1B). Comparatively, animals treated with the immunosuppression regimen of ATG, CSA and MMF maintained normoglycemia throughout their 90 day follow-up period and had an average fasting blood glucose of 59.4 mg/dl ±12.1 at day 5 post-transplant (FIG. 1). Animals that were pre-treated with exenatide also maintained normoglycemia. In fact, two animals in this group were followed for 435 days post-transplant and continued to maintain normoglycemia throughout this period (FIG. 1A). On day 5 post-transplant, the average fasting blood glucose for this group was 52.7 mg/dl±14.8 (FIG. 1B). Finally, animals treated with exenatide post-transplant only showed moderately elevated fasting blood glucose from day 4 post-transplant on (FIG. 1A), with an average fasting blood glucose on day 5 of 154 mg/dl±105 (FIG. 1B).

Figure 2:
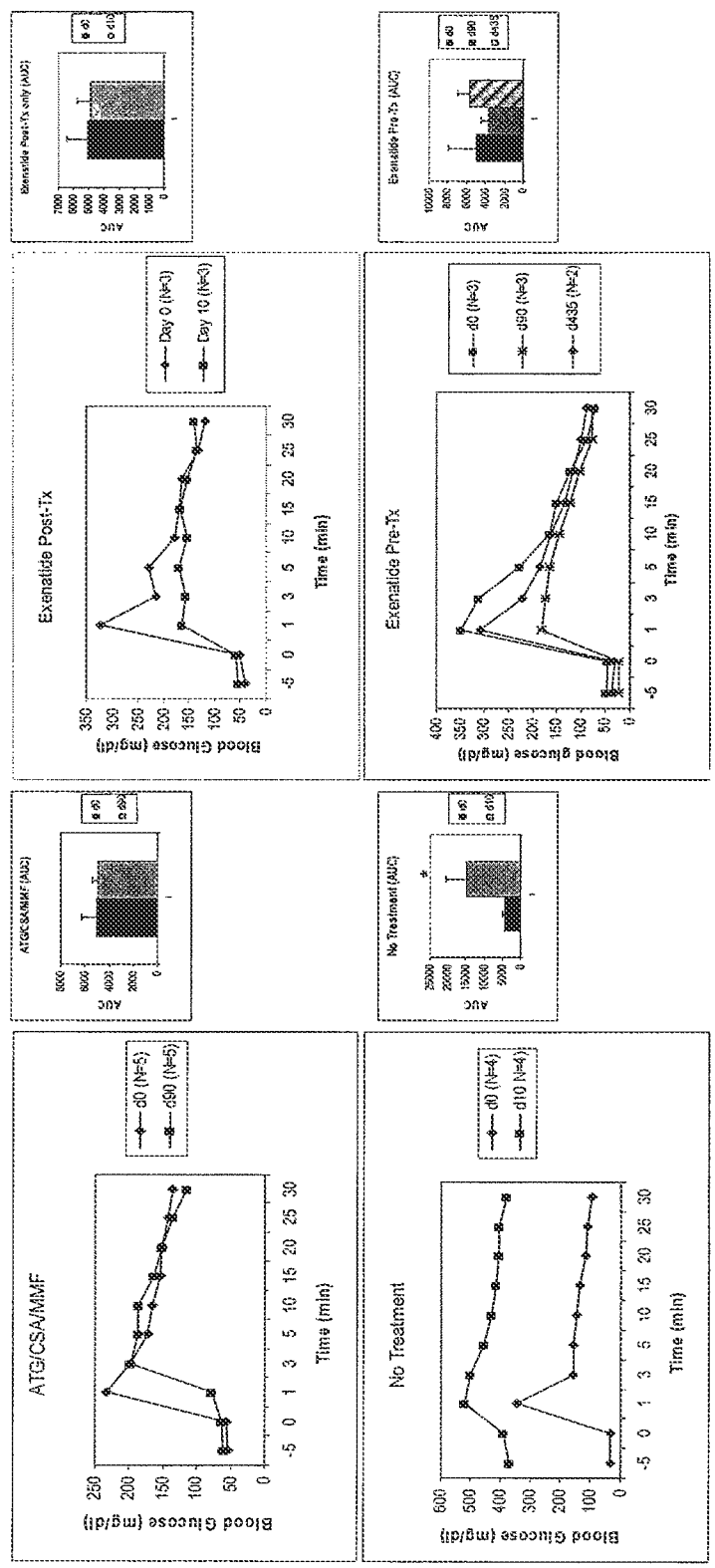
FIGS. 2A-B. Blood glucose levels measured following intravenous glucose administration (intravenous glucose tolerance test) with area under the curve measurements for glucose response (A). Serum insulin levels measured during intravenous glucose tolerance test as detected by ELISA (B). intravenous glucose tolerance tests were performed at baseline prior to pancreatectomy, at day 10 post-transplant for untreated and post-exenatide groups, and at day 90 post-transplant for ATG/CSA/MMF and exenatide pre-treatment groups. Animals pre-treated with exenatide or treated with ATG/CSA/MMF maintained glucose and insulin responses post-transplant that resembled that prior to pancreatectomy. Animals pre-treated with exenatide showed increased insulin production at both baseline and post-transplant compared to all other groups. Untreated recipients and animals receiving exenatide post-transplant only showed reduced insulin levels compared to baseline.
Figure 2:
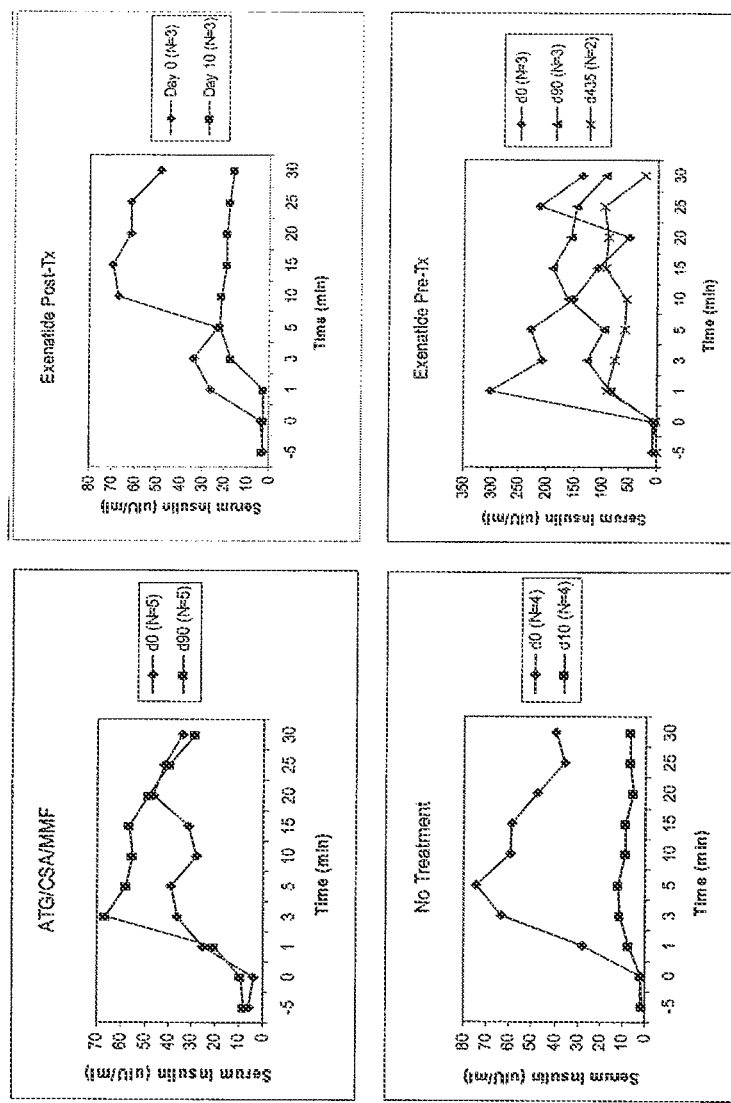

Intravenous Glucose Tolerance Tests:

intravenous glucose tolerance test results post-transplant were impaired in both untreated animals as well as animals treated with exenatide post-transplant only (FIG. 2). Blood glucose levels were significantly elevated in untreated animals with the AUC being significantly increased post-transplant. Animals treated with exenatide post-transplant only had an abnormal glucose curve although the AUC was not significantly different (FIG. 2A). Insulin curves post-transplant for both groups were abnormal compared to baseline with no noticeable $2^{nd}$ phase insulin production and severely reduced insulin levels (FIG. 2B). On the other hand, intravenous glucose tolerance tests for animals treated with ATG/CSA/MMF as well as animals pre-treated with exenatide were indicative of functional islet grafts, with blood glucose responses resembling that prior to pancreatectomy (FIG. 2A). There was no significant change post-transplant in the AUC for animals in these groups. Insulin levels actually increased post-transplant in the ATG/CSA/MMF group. For animals pre-treated with exenatide, there was some reduction in insulin over time post-transplant, however, insulin levels were still higher than that of any other treatment group. First and second phase insulin responses also continued to be noted post-transplant for both of these groups (FIG. 2B).

Figure 3:
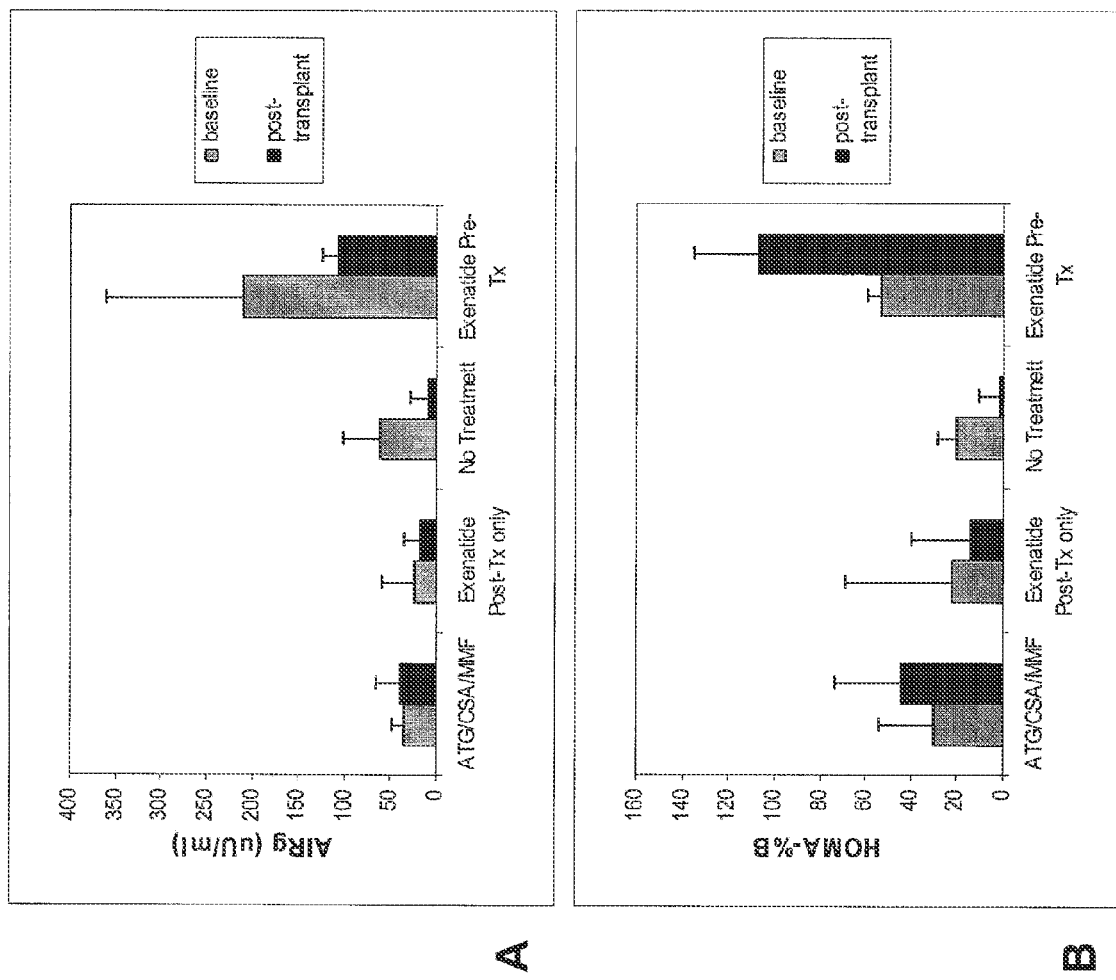
FIGS. 3A-B. Acute insulin response to glucose ($\mu$U/ml) as a measurement of first phase insulin secretion following i.v. glucose administration (A). Beta cell function as determined by homeostasis model assessment (HOMA-% B) (B). Untreated animals and animals treated with exenatide post-transplant only were tested at day 0 and at day 10. ATG/CSA/MMF and exenatide pre-treatment groups were tested at day 0 and day 90.

First phase insulin secretion (AIRg) in untreated recipients was severely reduced at 10 days post-transplant compared to baseline (9.53 μU/ml±19.2 vs. 61.0 μU/ml±40.0) (FIG. 3A). Beta cell function as determined by homeostasis model assessment (HOMA-% B) was also significantly reduced post-transplant in untreated animals (1.89%±9.14 vs. 20.2%±8.3 at baseline; p=0.01) (FIG. 3B). Islet recipients treated with exenatide post-transplant only had a mean AIRg at day 0 pre-pancreatectomy of 23.7 μU/ml±35.9. At 10 days post-transplant, this was reduced to 16.6 μU/ml±18.1 (FIG. 3A). Similarly, beta cell function also dropped post-transplant from 22.2%±46.4 at baseline to 13.8%±26.1 (FIG. 3B). On the other hand, recipients treated with ATG/CSA/MMF maintained a comparable first phase insulin secretion post-transplant. AIRg was 35.5 μU/ml±14.1 at baseline and continued at 39.7 μU/ml±26.6 ninety days post-transplant (FIG. 3A). Beta cell function increased slightly in this group although the difference was not significant. HOMA-% B in ATG/CSA/MMF-treated animals was 29.9%±24.3 at baseline and 43.8%±29.5 at day 90 (FIG. 3B). Animals that were pre-treated with exenatide showed notably higher first phase insulin secretion at baseline compared to all other groups (211 μU/ml±150). This did drop post-transplant to 105 μU/ml±19.0 at 90-days but continued to remain significantly higher than other treatment groups (FIG. 3A). Baseline beta cell function was also increased in the exenatide pre-treatment group compared to other groups (53.3%±5.55), and this actually showed a significant increase post-transplant to 107%±28.6 at 90 days (FIG. 3B).

In Vitro Glucose Stimulation:

The average stimulation index for islets isolated from animals receiving in vivo exenatide pre-treatment was 2.98±1.85. For islets isolated from untreated donor animals (not previously treated with exenatide), the average stimulation index was 0.52±0.32. This was significantly lower than that of exenatide-treated animals (p=0.04).

Discussion

Fasting blood glucose levels were used as a determinant for islet graft function post-transplant. Untreated recipients had an average fasting blood glucose on day 5 post-transplant of 265 mg/dl±172. Rejection was expected in these animals, and this hyperglycemia was indicative of graft failure. Animals receiving exenatide beginning on the day of transplant had an average fasting blood glucose at day 5 of 154 mg/dl±105. Animals in this group showed variable fasting blood glucose levels that remained somewhat elevated from day 4 post-transplant to endpoint. While fasting blood glucose levels were less severely elevated than those of untreated animals and did not consistently meet the criteria for diabetes determination (fasting blood glucose≥250 mg/dl), they remained elevated throughout the study. Comparatively, ATG/CSA/

MMF-treated animals as well as animals pre-treated with exenatide maintained normoglycemia following islet cell transplant, indicating functional islet grafts for the duration of the study. In fact, overall fasting blood glucose was significantly lower in animals pre-treated with exenatide compared to animals treated with ATG/CSA/MMF. The immunosuppression strategy employed in this study included the calcineurin inhibitor, cyclosporine, which has been shown to have diabetogenic properties. The use of exenatide in place of this immunosuppression regimen may have reduced the damaging effects of cyclosporine on islet cell function. In addition, these results suggest that exenatide alone is sufficient for the prevention of graft rejection.

Results from intravenous glucose tolerance tests also indicate functioning islet allografts in animals pre-treated with exenatide or treated with ATG/CSA/MMF, whereas untreated animals had elevated glucose levels and reduced insulin production. Animals receiving exenatide treatment post-transplant only also showed impaired insulin production and abnormal glucose curves. Second phase insulin responses were not noticeable in either untreated or exenatide post-only treatment groups. Islet cell transplant recipients treated with exenatide prior to transplant showed increased insulin production in response to glucose compared to recipients treated only with the immunosuppression regimen of ATG, CSA and MMF. First phase insulin secretion was also significantly higher in the exenatide pre-treatment group at 90 days post-transplant relative to the ATG/CSA/MMF group. Also, at 90 days post-transplant, animals treated with exenatide alone showed significantly improved beta cell function compared to ATG/CSA/MMF-treated animals. Thus, in addition to protecting islets from rejection, exenatide was actually able to improve graft function relative to regular immunosuppression.

Due to our experimental set-up, both donors and recipients in the exenatide pre-treatment group began treatment 2 days prior to transplant. In vitro glucose stimulation assays performed on freshly isolated islets in this study indicated a significant improvement in islet function for islets pre-treated with exenatide compared to those that did not receive exenatide treatment. This suggests that exenatide pre-treated islets were of a higher quality upon transplantation. Improved glucose tolerance, insulin secretion and beta cell function in animals pre-treated with exenatide supports this. Additionally, even at day 0 prior to transplantation, insulin secretion and glucose tolerance were better in exenatide pre-treated animals compared to other groups. Serum insulin levels produced in response to i.v. glucose administration were also significantly higher in animals pre-treated with exenatide. Because this improvement was noted even at day 0, this suggests that pre-treatment with exenatide may be key in improved graft function and protection over time. Animals treated with exenatide post-transplant only did not show the same improvements and/or maintenance of graft function compared to those receiving pre-treatment. In summary, we have shown in this study that exenatide can improve graft function relative to treatment with immunosuppression and that, in fact, exenatide treatment alone is sufficient in itself in protecting islet allografts from rejection. However, pre-treatment of donors and/or recipients appears to be necessary to achieve this level of graft function. When exenatide treatment of the recipient is not initiated until day 0 and transplanted islets are also untreated, graft function becomes impaired and more closely resembles that of grafts in untreated animals. This, along with its potential to protect islets from autoimmune attack, makes exenatide a useful treatment for long-term success in islet transplantation in type 1 diabetic patients.

What is claimed is:

1. A method for treating diabetes in a patient in need thereof, the method comprising:
   (i) administering a therapeutically effective amount of a GLP-1 receptor agonist compound to the patient for a period of time of 1 day to 1 month prior to allogeneic islet transplant; and
   (ii) transplanting allogeneic islets into the patient;
thereby treating the diabetes in the patient, wherein the patient is not administered an immunosuppressive drug or an immunosuppressive treatment regimen before, during, or after any step in the method.

2. The method of claim 1, wherein the patient is a human.

3. The method of claim 1, wherein the GLP-1 receptor agonist compound is an exendin, a GLP-1(7-37), or an analog thereof.

4. The method of claim 1, wherein the GLP-1 receptor agonist compound comprises the amino acid sequence as set forth in SEQ ID NO:1, 3, or 23.

5. The method of claim 1, wherein the GLP-1 receptor agonist compound is exenatide, lixisenatide, liraglutide, dulaglutide, albiglutide, or taspoglutide.

* * * * *

SEQUENCE LISTING

<160> NUMBER OF SEQ ID NOS: 45

<210> SEQ ID NO 1
<211> LENGTH: 39
<212> TYPE: PRT
<213> ORGANISM: Heloderma suspectum
<220> FEATURE:
<221> NAME/KEY: MISC_FEATURE
<223> OTHER INFORMATION: C-term amidated

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 39
<212> TYPE: PRT
<213> ORGANISM: Heloderma horridum
<220> FEATURE:
<221> NAME/KEY: MISC_FEATURE
<223> OTHER INFORMATION: C-term amidated

<400> SEQUENCE: 2

His Ser Asp Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 3
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 3

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser
        35

<210> SEQ ID NO 4
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 4

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly Pro Ser
            20                  25                  30

Ser Gly Ala Pro Pro Ser
        35

<210> SEQ ID NO 5
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 5

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn Gly Gly Pro Ser
            20                  25                  30

Ser Gly Ala Pro Pro Ser
        35

<210> SEQ ID NO 6
<211> LENGTH: 30
<212> TYPE: PRT

```
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 6

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly
            20                  25                  30

<210> SEQ ID NO 7
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 7

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn Gly Gly
            20                  25                  30

<210> SEQ ID NO 8
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 8

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn Gly Gly
            20                  25                  30

<210> SEQ ID NO 9
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 9

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn Gly Gly
            20                  25                  30

<210> SEQ ID NO 10
<211> LENGTH: 28
```

```
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term may or may not be amidated

<400> SEQUENCE: 10

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn
            20                  25

<210> SEQ ID NO 11
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term may or may not be amidated

<400> SEQUENCE: 11

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Asn
            20                  25

<210> SEQ ID NO 12
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term may or may not be amidated

<400> SEQUENCE: 12

His Gly Glu Gly Thr Phe Thr Ser Asp Leu Ser Lys Gln Leu Glu Glu
1               5                   10                  15

Glu Ala Val Arg Leu Phe Ile Glu Phe Leu Lys Asn
            20                  25

<210> SEQ ID NO 13
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<223> OTHER INFORMATION: C-term may or may not be amidated

<400> SEQUENCE: 13

His Gly Glu Gly Thr Phe Thr Ser Asp Leu Ser Lys Gln Leu Glu Glu
1               5                   10                  15

Glu Ala Ala Arg Leu Phe Ile Glu Phe Leu Lys Asn
            20                  25

<210> SEQ ID NO 14
```

-continued

```
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 14

His Gly Glu Gly Thr Phe Thr Ser Asp Leu Ser Lys Gln Leu Glu Glu
1               5                   10                  15

Lys Ala Ala Lys Glu Phe Ile Glu Phe Leu Lys Gln Gly Gly Pro Ser
            20                  25                  30

Ser Gly Ala Pro Pro Pro Ser
        35

<210> SEQ ID NO 15
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 15

His Gly Glu Gly Thr Phe Thr Ser Asp Leu Ser Lys Gln Leu Glu Glu
1               5                   10                  15

Lys Ala Ala Lys Glu Phe Ile Glu Trp Leu Lys Gln Gly Gly Pro Ser
            20                  25                  30

Ser Gly Ala Pro Pro Pro Ser
        35

<210> SEQ ID NO 16
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated
<220> FEATURE:
<221> NAME/KEY: MOD_RES
<222> LOCATION: (14)..(14)
<223> OTHER INFORMATION: Octyl-Gly

<400> SEQUENCE: 16

His Gly Glu Gly Thr Phe Thr Ser Asp Leu Ser Lys Gln Gly Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Ser
        35

<210> SEQ ID NO 17
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
```

```
<220> FEATURE:
<221> NAME/KEY: MISC_FEATURE
<223> OTHER INFORMATION: C-term may or may not be amidated
<220> FEATURE:
<221> NAME/KEY: MOD_RES
<222> LOCATION: (34)..(34)
<223> OTHER INFORMATION: Octyl-Gly

<400> SEQUENCE: 17

His Gly Glu Gly Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Ser Gly Ala Pro Pro Pro Ser
        35

<210> SEQ ID NO 18
<211> LENGTH: 37
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 18

His Gly Glu Phe Thr Phe Thr Ser Asp Leu Ser Lys Gln Leu Glu Glu
1               5                   10                  15

Glu Ala Val Arg Leu Phe Ile Glu Trp Leu Lys Gln Gly Gly Pro Ser
            20                  25                  30

Lys Glu Ile Ile Ser
35

<210> SEQ ID NO 19
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 19

His Gly Glu Phe Thr Phe Thr Ser Asp Leu Ser Lys Gln Leu Glu Glu
1               5                   10                  15

Lys Ala Ala Lys Glu Phe Ile Glu Trp Leu Lys Gln Gly Gly Pro Ser
            20                  25                  30

Ser Gly Ala Pro Pro Pro Ser
        35

<210> SEQ ID NO 20
<211> LENGTH: 39
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 20
```

```
His Gly Glu Gly Thr Phe Thr Ser Asp Leu Val Lys Ile Leu Glu Ala
1               5                   10                  15

Glu Ala Val Arg Lys Phe Ile Glu Phe Leu Lys Asn Gly Gly Pro Ser
            20                  25                  30

Ser Gly Ala Pro Pro Ser
        35

<210> SEQ ID NO 21
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 21

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Ser Lys
        35                  40

<210> SEQ ID NO 22
<211> LENGTH: 31
<212> TYPE: PRT
<213> ORGANISM: Homo sapiens
<220> FEATURE:
<221> NAME/KEY: MISC_FEATURE
<223> OTHER INFORMATION: C-term may or may not be amidated

<400> SEQUENCE: 22

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
            20                  25                  30

<210> SEQ ID NO 23
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 23

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg
            20                  25                  30

<210> SEQ ID NO 24
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
```

```
<223> OTHER INFORMATION: C-term may or may not be amidated
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (29)..(29)
<223> OTHER INFORMATION: Aib

<400> SEQUENCE: 24

His Xaa Glu Gly Thr Phe Thr Ser Asp Val Ser Ser Tyr Leu Glu Gly
1               5                   10                  15

Gln Ala Ala Arg Glu Phe Ile Ala Phe Leu Val Arg Xaa Arg
            20                  25                  30

<210> SEQ ID NO 25
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated
<220> FEATURE:
<221> NAME/KEY: MOD_RES
<222> LOCATION: (2)..(2)
<223> OTHER INFORMATION: Ala, Val, or Gly
<220> FEATURE:
<221> NAME/KEY: MOD_RES
<222> LOCATION: (16)..(16)
<223> OTHER INFORMATION: Gly, Lys, or Glu
<220> FEATURE:
<221> NAME/KEY: MOD_RES
<222> LOCATION: (17)..(17)
<223> OTHER INFORMATION: Gln or Lys
<220> FEATURE:
<221> NAME/KEY: MOD_RES
<222> LOCATION: (24)..(24)
<223> OTHER INFORMATION: Ala or Glu
<220> FEATURE:
<221> NAME/KEY: MOD_RES
<222> LOCATION: (27)..(27)
<223> OTHER INFORMATION: Val or Lys
<220> FEATURE:
<221> NAME/KEY: MOD_RES
<222> LOCATION: (28)..(28)
<223> OTHER INFORMATION: Lys, Asn, or Arg
<220> FEATURE:
<221> NAME/KEY: MOD_RES
<222> LOCATION: (30)..(30)
<223> OTHER INFORMATION: Arg or Gly
<220> FEATURE:
<221> NAME/KEY: MOD_RES
<222> LOCATION: (31)..(31)
<223> OTHER INFORMATION: Gly, His, Pro, or not present

<400> SEQUENCE: 25

His Xaa Glu Gly Thr Phe Thr Ser Asp Val Ser Ser Tyr Leu Glu Xaa
1               5                   10                  15

Xaa Ala Ala Lys Glu Phe Ile Xaa Trp Leu Xaa Xaa Gly Xaa Xaa
            20                  25                  30

<210> SEQ ID NO 26
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
```

```
<221> NAME/KEY: MISC_FEATURE
<223> OTHER INFORMATION: C-term may or may not be amidated

<400> SEQUENCE: 26

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Arg Gly Arg Gly
            20                  25                  30

<210> SEQ ID NO 27
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 27

His Ala Glu Gly Thr Phe Thr Ser Asp Val Ser Ser Tyr Leu Glu Gly
1               5                   10                  15

Gln Ala Ala Lys Glu Phe Ile Glu Trp Leu Val Lys Gly Arg Gly
            20                  25                  30

<210> SEQ ID NO 28
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 28

His Ala Glu Gly Thr Phe Thr Ser Asp Val Ser Ser Tyr Leu Glu Lys
1               5                   10                  15

Gln Ala Ala Lys Glu Phe Ile Ala Trp Leu Val Lys Gly Arg Gly
            20                  25                  30

<210> SEQ ID NO 29
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 29

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 30
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
```

```
-continued

<220> FEATURE:
<221> NAME/KEY: MISC_FEATURE
<223> OTHER INFORMATION: C-term may or may not be amidated

<400> SEQUENCE: 30

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly
            20                  25                  30

<210> SEQ ID NO 31
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 31

His Gly Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Gly
            20                  25                  30

<210> SEQ ID NO 32
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 32

His Val Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Gly
            20                  25                  30

<210> SEQ ID NO 33
<211> LENGTH: 31
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 33

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
            20                  25                  30

<210> SEQ ID NO 34
<211> LENGTH: 31
<212> TYPE: PRT
<213> ORGANISM: Artificial Sequence
<220> FEATURE:
<223> OTHER INFORMATION: Description of Artificial Sequence: Synthetic
```

```
        polypeptide
<220> FEATURE:
<221> NAME/KEY: MISC_FEATURE
<223> OTHER INFORMATION: C-term may or may not be amidated

<400> SEQUENCE: 34

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Pro
            20                  25                  30

<210> SEQ ID NO 35
<211> LENGTH: 31
<212> TYPE: PRT
<213> ORGANISM: Artificial Sequence
<220> FEATURE:
<223> OTHER INFORMATION: Description of Artificial Sequence: Synthetic
        polypeptide
<220> FEATURE:
<221> NAME/KEY: MISC_FEATURE
<223> OTHER INFORMATION: C-term may or may not be amidated

<400> SEQUENCE: 35

His Gly Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Pro
            20                  25                  30

<210> SEQ ID NO 36
<211> LENGTH: 31
<212> TYPE: PRT
<213> ORGANISM: Artificial Sequence
<220> FEATURE:
<223> OTHER INFORMATION: Description of Artificial Sequence: Synthetic
        polypeptide
<220> FEATURE:
<221> NAME/KEY: MISC_FEATURE
<223> OTHER INFORMATION: C-term may or may not be amidated

<400> SEQUENCE: 36

His Val Glu Gly Thr Phe Thr Ser Asp Val Ser Ser Tyr Leu Glu Glu
1               5                   10                  15

Gln Ala Ala Lys Glu Phe Ile Ala Trp Leu Lys Asn Gly Gly Pro
            20                  25                  30

<210> SEQ ID NO 37
<211> LENGTH: 30
<212> TYPE: PRT
<213> ORGANISM: Artificial Sequence
<220> FEATURE:
<223> OTHER INFORMATION: Description of Artificial Sequence: Synthetic
        polypeptide
<220> FEATURE:
<221> NAME/KEY: MISC_FEATURE
<223> OTHER INFORMATION: C-term may or may not be amidated

<400> SEQUENCE: 37

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 38
<211> LENGTH: 30
<212> TYPE: PRT
<213> ORGANISM: Artificial Sequence
<220> FEATURE:
```

<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 38

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly
            20                  25                  30

<210> SEQ ID NO 39
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 39

His Val Glu Gly Thr Phe Thr Ser Asp Val Ser Ser Tyr Leu Glu Glu
1               5                   10                  15

Gln Ala Ala Lys Glu Phe Ile Ala Trp Leu Val Asn Gly Gly
            20                  25                  30

<210> SEQ ID NO 40
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated

<400> SEQUENCE: 40

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Asn Gly Gly
            20                  25                  30

<210> SEQ ID NO 41
<211> LENGTH: 230
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (16)..(16)
<223> OTHER INFORMATION: Pro or Glu
<220> FEATURE:
<221> NAME/KEY: MOD_RES
<222> LOCATION: (17)..(17)
<223> OTHER INFORMATION: Phe, Val, or Ala
<220> FEATURE:
<221> NAME/KEY: MOD_RES
<222> LOCATION: (18)..(18)
<223> OTHER INFORMATION: Leu, Glu, or Ala
<220> FEATURE:
<221> NAME/KEY: MOD_RES
<222> LOCATION: (80)..(80)
<223> OTHER INFORMATION: Asn or Ala
<220> FEATURE:

```
<221> NAME/KEY: MOD_RES
<222> LOCATION: (230)..(230)
<223> OTHER INFORMATION: May or may not be present

<400> SEQUENCE: 41

Ala Glu Ser Lys Tyr Gly Pro Pro Cys Pro Pro Cys Pro Ala Pro Xaa
1               5                   10                  15

Xaa Xaa Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Xaa
65              70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Lys
225                 230

<210> SEQ ID NO 42
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: see specification as filed for detailed
      description of substitutions and preferred embodiments
<220> FEATURE:
<221> NAME/KEY: misc_feature
<222> LOCATION: (1)..(30)
<223> OTHER INFORMATION: This sequence may encompass 1-6 repeating
      "GGGGS" subunits

<400> SEQUENCE: 42

Gly Gly Gly Gly Ser Gly Gly Gly Gly Ser Gly Gly Gly Gly Ser
1               5                   10                  15

Gly Gly Gly Ser Gly Gly Gly Gly Ser Gly Gly Gly Gly Ser
            20                  25                  30

<210> SEQ ID NO 43
```

<211> LENGTH: 275
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 43

```
His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Gly Gly Gly
            20                  25                  30

Gly Gly Gly Ser Gly Gly Gly Ser Gly Gly Gly Ser Ala Glu
        35                  40                  45

Ser Lys Tyr Gly Pro Pro Cys Pro Pro Cys Pro Ala Pro Glu Ala Ala
 50                  55                  60

Gly Gly Pro Ser Val Phe Leu Phe Pro Pro Lys Pro Lys Asp Thr Leu
 65                  70                  75                  80

Met Ile Ser Arg Thr Pro Glu Val Thr Cys Val Val Val Asp Val Ser
                85                  90                  95

Gln Glu Asp Pro Glu Val Gln Phe Asn Trp Tyr Val Asp Gly Val Glu
            100                 105                 110

Val His Asn Ala Lys Thr Lys Pro Arg Glu Glu Gln Phe Asn Ser Thr
        115                 120                 125

Tyr Arg Val Val Ser Val Leu Thr Val Leu His Gln Asp Trp Leu Asn
130                 135                 140

Gly Lys Glu Tyr Lys Cys Lys Val Ser Asn Lys Gly Leu Pro Ser Ser
145                 150                 155                 160

Ile Glu Lys Thr Ile Ser Lys Ala Lys Gly Gln Pro Arg Glu Pro Gln
                165                 170                 175

Val Tyr Thr Leu Pro Pro Ser Gln Glu Glu Met Thr Lys Asn Gln Val
            180                 185                 190

Ser Leu Thr Cys Leu Val Lys Gly Phe Tyr Pro Ser Asp Ile Ala Val
        195                 200                 205

Glu Trp Glu Ser Asn Gly Gln Pro Glu Asn Asn Tyr Lys Thr Thr Pro
210                 215                 220

Pro Val Leu Asp Ser Asp Gly Ser Phe Phe Leu Tyr Ser Arg Leu Thr
225                 230                 235                 240

Val Asp Lys Ser Arg Trp Gln Glu Gly Asn Val Phe Ser Cys Ser Val
                245                 250                 255

Met His Glu Ala Leu His Asn His Tyr Thr Gln Lys Ser Leu Ser Leu
            260                 265                 270

Ser Leu Gly
        275
```

<210> SEQ ID NO 44
<211> LENGTH: 40
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<221> NAME/KEY: MISC_FEATURE
<223> OTHER INFORMATION: C-term OH or NH2
<220> FEATURE:
<221> NAME/KEY: MISC_FEATURE
<223> OTHER INFORMATION: see specification as filed for detailed description of substitutions and preferred embodiments
<220> FEATURE:

```
<221> NAME/KEY: MOD_RES
<222> LOCATION: (2)..(2)
<223> OTHER INFORMATION: D-Ala, Gly, Val, Leu, Ile, Ser, or Thr
<220> FEATURE:
<221> NAME/KEY: MOD_RES
<222> LOCATION: (16)..(16)
<223> OTHER INFORMATION: Gly, Glu, Asp, or Lys
<220> FEATURE:
<221> NAME/KEY: MOD_RES
<222> LOCATION: (27)..(27)
<223> OTHER INFORMATION: Val or Ile

<400> SEQUENCE: 44

His Xaa Glu Gly Thr Phe Thr Ser Asp Val Ser Ser Tyr Leu Glu Xaa
1               5                   10                  15

Gln Ala Ala Lys Glu Phe Ile Ala Trp Leu Xaa Lys Gly Gly Pro Ser
            20                  25                  30

Ser Gly Ala Pro Pro Pro Cys Cys
        35                  40

<210> SEQ ID NO 45
<211> LENGTH: 40
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MISC_FEATURE
<223> OTHER INFORMATION: C-term may or may not be amidated
<220> FEATURE:
<221> NAME/KEY: MISC_FEATURE
<223> OTHER INFORMATION: see specification as filed for detailed
      description of substitutions and preferred embodiments

<400> SEQUENCE: 45

His Val Glu Gly Thr Phe Thr Ser Asp Val Ser Ser Tyr Leu Glu Glu
1               5                   10                  15

Gln Ala Ala Lys Glu Phe Ile Ala Trp Leu Ile Lys Gly Gly Pro Ser
            20                  25                  30

Ser Gly Ala Pro Pro Pro Cys Cys
        35                  40
```